United States Patent [19]
Chapman

[11] Patent Number: 5,453,564
[45] Date of Patent: Sep. 26, 1995

[54] INBRED CORN LINE PHTE4

[75] Inventor: Michael A. Chapman, Madison Lake, Minn.

[73] Assignee: Pioneer Hi-Bred International, Inc., Des Moines, Iowa

[21] Appl. No.: 186,730

[22] Filed: Jan. 24, 1994

[51] Int. Cl.$^6$ .............................. A01M 5/00; A01M 4/00; C12N 5/04

[52] U.S. Cl. .................. 800/200; 800/250; 800/DIG. 56; 435/240.4; 435/240.49; 435/240.5; 47/58; 47/DIG. 1

[58] Field of Search .............................. 435/172.1, 172.3, 435/240.4, 240.49, 240.5; 536/27; 800/200, 250, DIG. 52, DIG. 56; 935/18; 47/58.03

[56] References Cited

U.S. PATENT DOCUMENTS

| | | |
|---|---|---|
| 4,812,599 | 3/1989 | Segebart . |
| 5,285,004 | 2/1994 | Ambrose .................................. 800/200 |

FOREIGN PATENT DOCUMENTS

| | | |
|---|---|---|
| 160390 | 6/1986 | European Pat. Off. . |

OTHER PUBLICATIONS

Conger, B. V., et al. (1987) "Somatic Embryogenesis From Cultured Leaf Segments of *Zea Mays*", *Plant Cell Reports*, 6:345–347.
Duncan, D. R., et al. (1985) "The Production of Callus Capable of Plant Regeneration From Immature Embryos of Numerous *Zea Mays* Genotypes", Planta, 165:322–332.
Edallo, et al. (1981) "Chromosomal Variation and Frequency of Spontaneous Mutation Associated with in vitro Culture and Plant Regeneration in Maize", *Maydica*, XXVI:39–56.
Green, et al., "Plant Regeneration From Tissue Cultures of Maize", *Crop Science*, vol. 15, pp. 417–421.
Green, C. E., et al. (1982) "Plant Regeneration in Tissue Cultures of Maize" *Maize for Biological Research*, pp. 367–372.
Hallauer, A. R. et al. (1988) "Corn Breeding" *Corn and Corn Improvement*, No. 18, pp. 463–481.
Meghji, M. R., et al. (1984). "Inbreeding Depression, Inbred & Hybrid Grain Yields, and Other Traits of Maize Genotypes Representing Three Eras", *Crop Science*, vol. 24, pp. 545–549.
Phillips, et al. (1988) "Cell/Tissue Culture and In Vitro Manipulation", *Corn & Corn Improvement*, 3rd Ed., ASA Publication, No. 18, pp. 345–349 & 356–357.
Poehlman (1987) *Breeding Field Crop*, AVI Publication Co., Westport, Conn., pp. 237–246.
Rao, K. V., et al., "Somatic Embryogenesis in Glume Callus Cultures", Osmania University, Hyberaded, India.
Sass, John F. (1977) "Morphology", *Corn & Corn Improvment*, ASA Publication Madison, Wisconsin, pp. 89–109.
Songstad, D. D. et al. (1988) "Effect of ACC (1–aminocyclopropane–1–carboxyclic acid), Silver Nitrate & Norbonadiene on Plant Regeneration From Maize Callus Cultures", *Plant Cell Reports*, 7:262–265.
Tomes, et al. "The Effect of Parental Genotype on Initiation of Embryogenic Callus From Elite Maize (*Zea Mays L.*) Germplasm", *Theor. Appl. Genet.*, vol. 70, pp. 505–509.
Troyer, et al. (1985) "Selection for Early Flowering in Corn: 10 Late Synthetics", *Crop Science*, vol. 25, pp. 695–697.
Umbeck, et al. "Reversion of Male–Sterile T–Cytoplasm Maize to Male Fertility in Tissue Culture", *Crop Science*, vol. 23, pp. 584–588.
Wright, Harold (1980) "Commercial Hybrid Seed Production", *Hybridization of Crop Plants*, Ch. 8: 161–176.
Wych, Robert D. (1988) "Production of Hybrid Seed", *Corn and Corn Improvement*, Ch. 9, pp. 565–607.
Green et al. 1975. Crop Science. 15:417–421.
Mallauer et al. 1988. In Corn and Corn Improvement. Sprague et al., eds. CH 8: 463–564.
Meghji et al. 1984. Crop Science. 24: 545–549.
Wright. 1980. In Hybridization of Crop Plants. Fehr et al., eds. Ch. 8: 161–176.
Wych. 1988. In Corn and Corn Improvement. Sprague et al., eds. CH. 9: 565–607.

*Primary Examiner*—Gary Benzion
*Assistant Examiner*—Erich E. Veitenheimer
*Attorney, Agent, or Firm*—Pioneer Hi-Bred International, Inc.

[57] ABSTRACT

According to the invention, there is provided an inbred corn line, designated PHTE4. This invention thus relates to the plants and seeds of inbred corn line PHTE4 and to methods for producing a corn plant produced by crossing the inbred line PHTE4 with itself or with another corn plant. This invention further relates to hybrid corn seeds and plants produced by crossing the inbred line PHTE4 with another corn line or plant.

9 Claims, 2 Drawing Sheets

INBRED CORN LINE PHTE4

FIELD OF THE INVENTION

This invention is in the field of corn breeding, specifically relating to an inbred corn line designated PHTE4.

BACKGROUND OF THE INVENTION

Plant Breeding

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Corn plants (*Zea mays* L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of a hybrid corn variety involves three steps: (1) the selection of plants from various germplasm pools; (2) the selfing of the selected plants for several generations to produce a series of inbred lines, which, although different from each other, breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny. An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

The objective of commercial maize inbred line development programs is to develop new inbred lines that combine to produce high grain yields and superior agronomic performance in hybrid combination. The primary trait breeders seek is yield. However, other major agronomic traits are of importance in hybrid combination and have an impact on yield or otherwise provide superior performance in hybrid combinations. Such traits include percent grain moisture at harvest, relative maturity, resistance to stalk breakage, resistance to root lodging, grain quality, and disease and insect resistance. In addition the lines per se must have acceptable performance for parental traits such as seed yields, kernel sizes, pollen production, all of which affect ability to provide parental lines in sufficient quantity and quality for hybridization. Traits have been shown to be under genetic control and many if not all of the traits are affected by multiple genes. Thus, to be selected as an inbred line, the inbred must be able to combine such that the desired traits are passed to the hybrid and also be able to satisfy production requirements as a parental line.

Pedigree Breeding

The pedigree method of breeding is the mostly widely used methodology for new inbred line development.

In general terms this procedure consists of crossing two inbred lines to produce the non-segregating $F_1$ generation, and self pollination of the $F_1$ generation to produce the $F_2$ generation that segregates for all factors for which the inbred parents differ. An example of this process is set forth below. Variations of this generalized pedigree method are used, but all these variations produce a segregating generation which contains a range of variation for the traits of interest.

EXAMPLE 1

Hypothetical example of pedigree breeding program

Consider a cross between two inbred lines that differ for alleles at five loci.

The parental genotypes are:

| Parent 1 | A | b | C | d | e | F/A | b | C | d | e | F |
|----------|---|---|---|---|---|-----|---|---|---|---|---|
| Parent 2 | a | B | c | D | E | f/a | B | c | D | E | f | the $F_1$ from a cross between these two parents is:

| $F_1$ | A | b | C | d | e | F/a | B | c | D | E | f |
|-------|---|---|---|---|---|-----|---|---|---|---|---|

Selfing $F_1$ will produce an $F_2$ generation including the following genotypes:

| A | b | c | D | E | f/a | b | C | d | e | F |
|---|---|---|---|---|-----|---|---|---|---|---|
| A | B | c | D | e | f/a | b | C | d | E | F |
| A | B | c | D | e | f/a | b | C | d | e | F |

The number of genotypes in the $F_2$ is $3^6$ for six segregating loci (729) and will produce $(2^6)-2$ possible new inbreds, (62 for six segregating loci).

Each inbred parent which is used in breeding crosses represents a unique combination of genes, and the combined effects of the genes define the performance of the inbred and its performance in hybrid combination. There is published evidence (Smith, O. S., J. S. C. Smith, S. L. Bowen, R. A. Tenborg and S. J. Wall, TAG 80:833–840 (1990)) that each of these lines are different and can be uniquely identified on the basis of genetically-controlled molecular markers.

It has been shown (Hallauer, Arnel R. and Miranda, J. B. Fo. *Quantitative Genetics in Maize Breeding*, Iowa State University Press, Ames Iowa (1981)) that most traits of economic value in maize are under the genetic control of multiple genetic loci, and that there are a large number of unique combinations of these genes present in elite maize germplasm. If not, genetic progress using elite inbred lines would no longer be possible. Studies by Duvick and Russell (Duvick, D. N. *Maydica* 37:69–79 (1992); Russell, W. A. *Maydica* XXIX:375–390 (1983)) have shown that over the last 50 years the rate of genetic progress in commercial hybrids has been between 1 and 2% per year.

The number of genes affecting the trait of primary economic importance in maize, grain yield, has been estimated to be in the range of 10–1000. Inbred lines which are used as parents for breeding crosses differ in the number and combination of these genes. These factors make the plant breeder's task more difficult. Compounding this is evidence that no one line contains the favorable allele at all loci, and that different alleles have different economic values depending on the genetic background and field environment in which the hybrid is grown. Fifty years of breeding experience shows that there are many genes affecting grain yield and each of these has a relatively small effect on this trait. The effects are small compared to breeders' ability to measure grain yield differences in evaluation trials. Therefore, the parents of the breeding cross must differ at several of these loci so that the genetic differences in the progeny will be large enough that breeders can develop a line that increases the economic worth of its hybrids over that of hybrids made with either parent.

If the number of loci segregating in a cross between two inbred lines is n, the number of unique genotypes in the $F_2$ generation is $3^n$ (Example 2) and the number of unique inbred lines from this cross is $\{(2^n)-2\}$. Only a very limited number of these combinations are useful. Only about 1 in 10,000 of the progeny from $F_2$'s are commercially useful.

By way of example, if it is assumed that the number of segregating loci in $F_2$ is somewhere between 20 and 50, and that each parent is fixed for half the favorable alleles, it is then possible to calculate approximate probabilities of finding an inbred that has the favorable allele at $\{(n/2)+m\}$ loci, where n/2 is the number of favorable alleles in each of the parents and m is the number of additional favorable alleles in the new inbred. See Example 2 below. The number m is assumed to be greater than three because each allele has so small an effect that evaluation techniques are not sensitive enough to detect differences due to three or less favorable alleles. The probabilities in Example 2 are on the order of $10^{-5}$ or smaller and they are the probabilities that at least one genotype with (n/2)+m favorable alleles will exist.

To put this in perspective the number of plants grown on 60 million acres (approximate U.S. corn acreage) at 25000 plants/acre is $1.5 \times 10^{12}$.

EXAMPLE 2

Probability of finding an inbred with m of n favorable alleles.

Assume each parent has n/2 of the favorable alleles and only ½ of the combinations of loci are economically useful.

| no. of segregating loci (n) | no. favorable alleles in Parents (n/2) | no. additional favorable alleles in new inbred | Probability that genotype occurs* |
|---|---|---|---|
| 20 | 10 | 14 | $3 \times 10^{-5}$ |
| 24 | 12 | 16 | $2 \times 10^{-5}$ |
| 28 | 14 | 18 | $1 \times 10^{-5}$ |
| 32 | 16 | 20 | $8 \times 10^{-6}$ |
| 36 | 18 | 22 | $5 \times 10^{-6}$ |
| 40 | 20 | 24 | $3 \times 10^{-6}$ |
| 44 | 22 | 26 | $2 \times 10^{-6}$ |
| 48 | 24 | 28 | $1 \times 10^{-6}$ |

*Probability that a useful combination exists, does not include the probability of identifying this combination if it does exist.

The possibility of having a usably high probability of being able to identify this genotype based on replicated field testing would be most likely smaller than this, and is a function of how large a population of genotypes is tested and how testing resources are allocated in the testing program.

At Pioneer Hi-Bred International, a typical corn research station has a staff of four, and 20 acres of breeding nursery. Those researchers plant those 20 acres with 25,000 nursery rows, 15,000 yield test plots in 10–15 yield test sites, and one or two disease-screening nurseries. Employing a temporary crew of 20 to 30 pollinators, the station makes about 65,000 hand pollinations per growing season. Thus, one of the largest plant breeding programs in the world does not have a sufficiently large breeding population to be able to rely upon "playing the numbers" to obtain successful research results. Nevertheless, Pioneer's breeders at each station produce from three to ten new inbreds which are proposed for commercial use each year. Over the 32 Pioneer research stations in North America, this amounts to from about 100 to 300 new inbreds proposed for use, and less than 50 and more commonly less than 30 of these inbreds that actually satisfy the performance criteria for commercial use.

This is a result of plant breeders using their skills, experience and intuitive ability to select inbreds having the necessary qualities.

SUMMARY OF THE INVENTION

According to the invention, there is provided a novel inbred corn line, designated PHTE4. This invention thus relates to the seeds of inbred corn line PHTE4, to the plants of inbred corn line PHTE4, and to methods for producing a corn plant produced by crossing the inbred line PHTE4 with itself or another corn line. This invention further relates to hybrid corn seeds and plants produced by crossing the inbred line PHTE4 with another corn line.

DEFINITIONS

In the description and examples that follow, a number of terms are used herein. In order to provide a clear and consistent understanding of the specification and claims, including the scope to be given such terms, the following definitions are provided. ABS is in absolute terms and % MN is percent of the mean for the experiments in which the inbred or hybrid was grown.

BAR PLT=BARREN PLANTS. The percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Actual yield of the grain at harvest in bushels per acre adjusted to 15.5% moisture.

DRP EAR=DROPPED EARS. A measure of the number of dropped ears per plot and represents the percentage of plants that did not drop ears prior to harvest.

EAR HT=EAR HEIGHT. The ear height is a measure from the ground to the highest placed developed ear node attachment and is measured in inches.

EAR SZ=EAR SIZE. A 1 to 9 visual rating of ear size. The higher the rating the larger the ear size.

EST CNT=EARLY STAND COUNT. This is a measure of the stand establishment in the spring and represents the number of plants that emerge on a per plot basis for the inbred or hybrid.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GRN APP=GRAIN APPEARANCE. This is a 1 to 9 rating for the general appearance of the shelled grain as it is harvested based on such factors as the color of the harvested grain, any mold on the grain, and any cracked grain. High scores indicate good grain quality.

MST=HARVEST MOISTURE. The moisture is the actual percentage moisture of the grain at harvest.

PLT HT=PLANT HEIGHT. This is a measure of the height of the plant from the ground to the tip of the tassel in inches.

POL SC=POLLEN SCORE. A 1 to 9 visual rating indicating the amount of pollen shed. The higher the score the more pollen shed.

POL WT=POLLEN WEIGHT. This is calculated by dry weight of tassels collected as shedding commences minus dry weight from similar tassels harvested after shedding is complete.

It should be understood that the inbred can, through routine manipulation of cytoplasmic factors, be produced in a cytoplasmic male-sterile form which is otherwise phenotypically identical to the male-fertile form.

PRM=PREDICTED RM. This trait, predicted relative maturity (RM), is based on the harvest moisture of the grain. The relative maturity rating is based on a known set of checks and utilizes standard linear regression analyses and is referred to as the Comparative Relative Maturity Rating System which is similar to the Minnesota Relative Maturity Rating System.

RT LDG=ROOT LODGING. Root lodging is the percentage of plants that do not root lodge; plants that lean from the vertical axis at an approximately 30° angle or greater would be counted as root lodged.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS=TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT (UNADJUSTED). The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

MDM CPX=Maize Dwarf Mosaic Complex (MDMV= Maize Dwarf Mosaic Virus & MCDV=Maize Chlorotic Dwarf Virus): Visual rating (1–9 score) where a "1" is very susceptible and a "9" is very resistant.

SLF BLT=Southern Leaf Blight (*Bipolaris maydis, Helminthosporium maydis*): Visual rating (1–9 score) where a "1" is very susceptible and a "9" is very resistant.

NLF BLT=Northern Leaf Blight (*Exserohilum turcicum, H. turcicum*): Visual rating (1–9 score) where a "1" is very susceptible and a "9" is very resistant.

COM RST=Common Rust (*Puccinia sorghi*): Visual rating (1–9 score) where a "1" is very susceptible and a "9" is very resistant.

GLF SPT=Gray Leaf Spot (*Cercospora zeae-maydis*): Visual rating (1–9 score) where a "1" is very susceptible and a "9" is very resistant.

STW WLT=Stewart's Wilt (*Erwinia stewartii*): Visual rating (1–9 score) where a "1" is very susceptible and a "9" is very resistant.

HD SMT=Head Smut (*Sphacelotheca reiliana*): Percentage of plants that did not have infection.

EAR MLD=General Ear Mold: Visual rating (1–9 score) where a "1" is very susceptible and a "9" is very resistant. This is based on overall rating for ear mold of mature ears without determining specific mold organism, and may not be predictive for a specific ear mold.

ECB DPE=Dropped ears due to European Corn Borer (*Ostrinia nubilalis*): Percentage of plants that did not drop ears under second brood corn borer infestation.

ECB 2SC=European Corn Borer Second Brood (*Ostrinia nubilalis*): Visual rating (1–9 score) of post flowering damage due to infestation by European Corn Borer. A "1" is very susceptible and a "9" is very resistant.

ECB 1LF=European Corn Borer First Brood (*Ostrinia*

*nubilalis*): Visual rating (1–9 score) of pre-flowering leaf feeding by European Corn Borer. A "1" is very susceptible and a "9" is very resistant.

DETAILED DESCRIPTION OF THE INVENTION

PHTE4 produces hybrids that are high yielding and flower early. PHTE4 hybrids have above average seedling vigor, test weight and staygreen. PHTE4 hybrids also have above average resistance to brittle stalks.

Inbred corn line PHTE4 is a yellow, dent corn inbred that provides an acceptable male parental line in crosses for producing first generation F1 corn hybrids. PHTE4 also provides an acceptable female parental line in crosses for producing first generation F1 corn hybrids. PHTE4 is adapted to the North Central region of the United States.

The inbred has shown uniformity and stability within the limits of environmental influence for all the traits as described in the Variety Description Information (Table 1) that follows. Most of the data in the Variety Description information was collected at Johnston, Iowa. The inbred has been self-pollinated and ear-rowed a sufficient number of generations with careful attention paid to uniformity of plant type to ensure homozygosity and phenotypic stability. The line has been increased both by hand and in isolated fields with continued observation for uniformity. No variant traits have been observed or are expected in PHTE4.

Inbred corn line PHTE4, being substantially homozygous, can be reproduced by planting seeds of the line, growing the resulting corn plants under self-pollinating or sib-pollinating conditions with adequate isolation, and harvesting the resulting seed, using techniques familiar to the agricultural arts.

TABLE 1

VARIETY DESCRIPTION INFORMATION
INBRED = PHTE4
Type: Dent    Region Best Adapted: North Central A. Maturity: Average across maturity zones.

Heat Unit Shed: 1340
Heat Unit Silk: 1330
No. Reps: 35

$$\text{HEAT UNITS} = \frac{[\text{Max. Temp.} (\leq 86° \text{F.}) + \text{Min. Temp} (\geq 50° \text{F.})]^*}{2} - 50$$

*If maximum is greater than 86 degrees fahrenheit, then 86 is used and if minimum is less than 50, then 50 is used. Heat units accumulated daily and can not be less than 0.

B. Plant Characteristics:

Plant height (to tassel tip): 207 cm
Length of top ear internode: 10 cm
Number of ears per stalk: Slight, two-ear tendency
Ear height (to base of top ear): 66 cm
Number of tillers: None
Cytoplasm type: Normal C. Leaf:

Color: (B14) Dark Green
Angle from Stalk: 30–60 degrees
Marginal Waves: (WF9) Few
Number of Leaves (mature plants): 19

TABLE 1-continued

VARIETY DESCRIPTION INFORMATION
INBRED = PHTE4
Type: Dent    Region Best Adapted: North Central Sheath Pubescence: (W22) Light
Longitudinal Creases: (PA11) Many
Length (Ear node leaf): 64 cm
Width (widest point, ear node leaf): 7 cm D. Tassel:

Number lateral branches: 3
Branch Angle from central spike: >45 degrees
Pollen Shed: Heavy based on Pollen Yield Test (108% of experiment means)
Peduncle Length (top leaf to basal branches): 21 cm
Anther Color: Purple
Glume Color: Green E. Ear (Husked Ear Data Except When Stated Otherwise):

Length: 14 cm
Weight: 127 gm
Mid-point Diameter: 42 mm
Silk Color: Green
Husk Extension (Harvest stage): Long (8–10 cm beyond ear tip)
Husk Leaf: short (<8 cm)
Taper of Ear: Average
Position of Shank (dry husks): Upright
Kernel Rows: Straight, Distinct Number = 14
Husk Color (fresh): Light Green
Husk Color (dry): Buff
Shank Length: 10 cm
Shank (No. of internodes): 8

F. Kernel (Dried):

Size (from ear mid-point)
Length:    11 mm
Width:     8 mm
Thick:     4 mm
Shape Grade (% rounds): <20 (18% medium round based on Parent Test Data)
Pericarp Color: Colorless
Aleurone Color: Homozygous Yellow
Endosperm Color: Yellow
Endosperm Type: Normal Starch
Gm Wt/100 Seeds (unsized): 27 gm G. Cob:

Diameter at mid-point: 22 mm
Strength: Strong
Color: Red

H. Diseases:

Corn Lethal Necrosis (MCMV = Maize Chlorotic Mottle Virus and MDMV = Maize Dwarf Mosaic Virus): Resistant
Carbonum Leaf Blight (*H. carbonum*): Resistant
N. Leaf Blight (*E. turcicum*): Intermediate
Common Rust (*P. sorghi*): Resistant
Gray Leaf Spot (*C. zeae*): Susceptible
Stewart's Wilt (*E. stewartii*): Resistant
Goss's Wilt (*C. Nebraskense*) Intermediate
Common Smut (*U. maydis*): Highly Resistant
Head Smut (*S. reiliana*) Highly Resistant
Fusarium Ear Mold (*F. moniliforme*): Intermediate
Gibberella Ear Rot (*G. zeae*): Intermediate I. Insects:

European Corn Borer-1 Leaf Damage (Preflowering): Resistant
European Corn Borer-2 (Post-flowering): Intermediate
The above descriptions are based on a scale of 1-9, 1 being highly susceptible, 9 being highly resistant.
S (Susceptible): Would generally represent a score of 1–3.
I (Intermediate): Would generally represent a score of 4–5.
R (Resistant): Would generally represent a score of 6–7.
H (Highly Resistant): Would generally represent a score of 8–9. Highly resistant does not imply the inbred is

TABLE 1-continued

VARIETY DESCRIPTION INFORMATION
INBRED = PHTE4
Type: Dent    Region Best Adapted: North Central immune.
J. Variety Most Closely Resembling:

| Character | Inbred |
|---|---|
| Maturity | PHBW8 |
| Usage | PHBW8 |

PHBW8 (PVP Certificate No. 9200079) is a Pioneer Hi-Bred International, Inc. proprietary inbred.
Data for Items B, C, D, E, F, and G is based primarily on a maximum of two reps from Johnston, Iowa grown in 1992, plus description information from the maintaining station.

ELECTROPHORESIS RESULTS

Isozyme Genotypes for PHTE4

Isozyme data were generated for inbred corn line PHTE4 according to the procedures described in Stuber, C. W., Wendel, J. F., Goodman, M. M., and Smith, J. S. C., "Techniques and Scoring Procedures for Starch Gel Electrophoresis of Enzymes from Maize (*Zea mays* L.)", Technical Bulletin No. 286, North Carolina Agricultural Research Service, North Carolina State University, Raleigh, N.C. (1988).

The data in Table 2 compares PHTE4 with its parents, PHN15 and PHJ40.

TABLE 2

ELECTROPHORESIS RESULTS FOR PHTE4
AND ITS PARENTS PHN15 AND PHJ40

| | | PARENTS | |
|---|---|---|---|
| LOCI | PHTE4 | PHN15 | PHJ40 |
| ACP1 | 2 | 4 | 2 |
| ADH1 | 4 | 4 | 4 |
| CAT3 | 9 | 9 | 9 |
| DIA1 | 8 | 8 | 8 |
| GOT1 | 4 | 4 | 4 |
| GOT2 | 4 | 4 | 4 |
| GOT3 | 4 | 4 | 4 |
| IDH1 | 4 | 4 | 4 |
| IDH2 | 6 | 6 | 6 |
| MDH1 | 6 | 6 | 6 |
| MDH2 | 6 | 3.5 | 6 |
| MDH3 | 16 | 16 | 16 |
| MDH4 | 12 | 12 | 12 |
| MDH5 | 12 | 12 | 12 |
| MMM | 4 | 4 | 4 |
| PGM1 | 9 | 9 | 9 |
| PGM2 | 4 | 4 | 4 |
| PGD1 | 3.8 | 2 | 3.8 |
| PGD2 | 5 | 5 | 5 |
| PHI1 | 4 | 4 | 4 |

EXAMPLES

Inbred and Hybrid Performance of PHTE4

In the examples that follow, the traits and characteristics of inbred corn line PHTE4 are given as a line in comparison with other inbreds and in hybrid combination. The data collected on inbred corn line PHTE4 is presented for the key characteristics and traits.

Table 3A compares PHTE4 to PHN15. PHTE4 has lower yield and grain harvest moisture but higher test weight compared to PHN15. PHTE4 is a shorter inbred and flowers (GDU Shed and GDU Silk) earlier than PHN15.

The data in Table 3B shows PHTE4 has lower yield and higher grain harvest moisture than PHNV4. PHTE4 and PHNV4 have similar plant height but PHTE4 has lower ear placement. PHTE4 is an earlier flowering (GDU Shed and GDU Silk) inbred compared to PHNV4.

Table 3C compares PHTE4 to PHJ40. PHTE4 has higher yield and grain harvest moisture but lower test weight compared to PHJ40. PHTE4 has a larger ear and is taller with lower ear placement compared to PHJ40. PHTE4 flowers (GDU Shed and GDU Silk) later than PHJ40. PHTE4 has greater pollen weight than PHJ40. PHTE4 has fewer scattergrain, better staygreen and better resistance to ear mold and first brood European corn borer than PHJ40.

The data in Table 3D shows PHTE4 has a higher yield than PHT46. PHTE4 has a larger ear and is taller with higher ear placement compared to PHT46. PHTE4 flowers (GDU Shed and GDU Silk) later than PHT46. PHTE4 has a significantly greater pollen weight than PHT46. PHTE4 has better ear texture and staygreen with better resistance to first and second brood European corn borer compared to PHT46.

Table 3E shows PHTE4 has lower yield and grain harvest moisture but higher test weight compared to PHBW8. PHTE4 and PHBW8 have similar ear placement but PHTE4 is a taller inbred. PHTE4 and PHBW8 shed (GDU Shed) pollen at approximately at the same time but PHTE4 silks (GDU Silk) earlier than PHBW8. PHTE4 has better first brood European corn borer resistance than PHBW8.

Table 4A compares PHTE4 to PHNV4 when both were crossed to the same inbred testers. The PHTE4 hybrids have higher yield and grain harvest moisture compared to the PHNV4 hybrids. The PHTE4 hybrids have better seedling vigor and higher early stand count than the PHNV4 hybrids. The PHTE4 hybrids are shorter with lower ear placement compared to the PHNV4 hybrids.

Table 4B compares PHTE4 to PHRE1 when both were crossed to the same inbred testers. The hybrids yield similarly but the PHTE4 hybrids have higher grain harvest moisture than the PHRE1 hybrids. The PHTE4 hybrids have better seedling vigor than the PHRE1 hybrids.

Table 4C compares PHTE4 to PHBW8 when both were crossed to the same inbred testers. The PHTE4 hybrids have lower yield and grain harvest moisture compared to the PHBW8 hybrids. The PHTE4 hybrids have better grain appearance and seedling vigor than the PHBW8 hybrids.

Table 5A compares PHTE4 to PHBW8 when both were crossed to the same inbred. The hybrids have similar yield and test weight but the PHTE4 hybrid has lower grain harvest moisture. The PHTE4 hybrid is taller with higher ear placement compared to the PHBW8 hybrid.

Table 5B compares PHTE4 to PHRE1 when both were crossed to the same inbred. The hybrids yield similarly but the PHTE4 hybrid has significantly higher grain harvest moisture than the PHRE1 hybrid. The PHTE4 hybrid has better test weight than the PHRE1 hybrid. The hybrids are similar in height but the PHTE4 hybrid has lower ear placement.

BRIEF DESCRIPTION OF THE DRAWINGS

Figure 1:
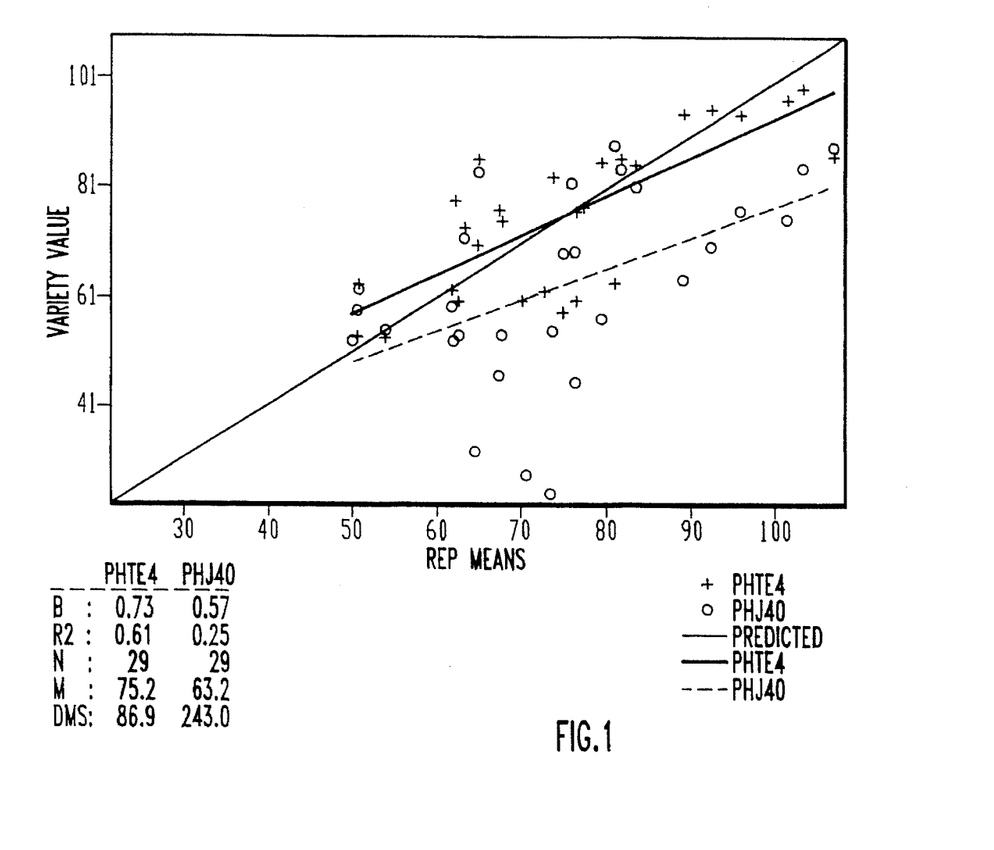
FIGS. 1 and 2 show data for the trait Bushels Per Acre. The results of FIGS. 1 and 2 compare PHTE4 to PHJ40 and PHBW8, respectively.

FIG. 1 compares the yield of PHTE4 and PHJ40. PHTE4 is higher yielding across all environments compared to PHJ40. PHTE4 has above average yield in low yield environments but below average yield in high yield environments whereas PHJ40 has below average yield over all environments.

Figure 2:
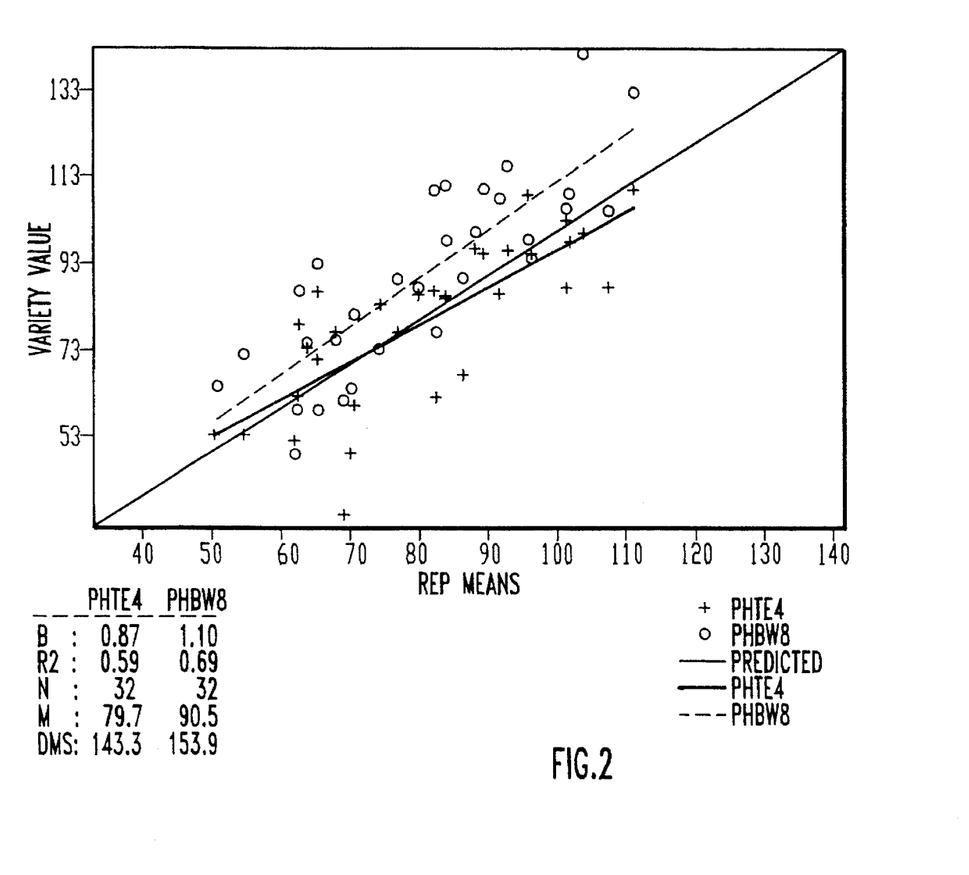

FIG. 2 compares the yield of PHTE4 and PHBW8.

PHTE4 is lower yielding than PHBW8 but the differential is less in low yield environments.

TABLE 3A

PAIRED INBRED COMPARISON DATA
VARIETY #1-PHTE4
VARIETY #2-PHN15

* = 10% SIG   + = 5% SIG   # = 1% SIG

| DEPT | VAR # | BU ACR ABS | BU ACR % MN | YLD SC ABS | MST MST ABS | EAR SZ ABS | BAR PLT ABS | PLT HT ABS | EAR HT ABS | SDG VGR ABS | EST CNT ABS |
|---|---|---|---|---|---|---|---|---|---|---|---|
| TOTAL SUM | 1 | 91.0 | 100 | 5.0 | 21.9 | 4.0 | 98.0 | 81.3 | 28.5 | 7.2 | 54.3 |
|  | 2 | 110.1 | 112 | 5.0 | 23.9 | 6.0 | 99.5 | 88.2 | 28.5 | 6.8 | 55.2 |
|  | LOCS | 3 | 3 | 1 | 3 | 1 | 5 | 3 | 3 | 5 | 3 |
|  | REPS | 6 | 6 | 1 | 6 | 1 | 8 | 5 | 5 | 8 | 6 |
|  | DIFF | 19.1 | 21 | 0.0 | 2.0 | 2.0 | 1.5 | 6.8 | 0.0 | 0.4 | 0.8 |
|  | PROB | .005# | .013+ |  | .026+ |  | .241 | .059* | .000# | .405 | .338 |

| DEPT | VAR # | TIL LER ABS | GDU SHD ABS | GDU SLK ABS | POL SC ABS | TAS SZ ABS | TST WT ABS | SCT GRN ABS | STA GRN ABS | STK LDG ABS | ECB 1LF ABS |
|---|---|---|---|---|---|---|---|---|---|---|---|
| TOTAL SUM | 1 | 1.3 | 1280 | 1295 | 5.0 | 4.0 | 60.1 | 7.0 | 4.7 | 90.5 | 7.0 |
|  | 2 | 0.3 | 1343 | 1360 | 5.0 | 3.0 | 57.3 | 7.0 | 5.7 | 81.8 | 6.0 |
|  | LOCS | 4 | 3 | 2 | 1 | 2 | 3 | 1 | 3 | 4 | 1 |
|  | REPS | 7 | 4 | 2 | 1 | 2 | 6 | 1 | 6 | 7 | 1 |
|  | DIFF | 1.0 | 63 | 65 | 0.0 | 1.0 | 2.8 | 0.0 | 1.0 | 8.7 | 1.0 |
|  | PROB | .525 | .109+ | .144 |  | .500 | .075* |  | .074* | .408 |  |

TABLE 3B

PAIRED INBRED COMPARISON DATA
VARIETY #1-PHTE4
VARIETY #2-PHNV4

* = 10% SIG   + = 5% SIG   # = 1% SIG

| DEPT | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | TIL LER ABS | GDU SHD ABS | GDU SLK ABS |
|---|---|---|---|---|---|---|---|---|---|---|---|---|---|---|
| TOTAL SUM | 1 | 76.7 | 100 | 6.0 | 32.7 | 6.0 | 94.6 | 78.3 | 30.5 | 5.9 | 33.6 | 4.3 | 1203 | 1198 |
|  | 2 | 97.5 | 126 | 6.0 | 27.5 | 5.0 | 93.3 | 80.3 | 35.3 | 7.0 | 31.7 | 1.4 | 1224 | 1239 |
|  | LOCS | 1 | 1 | 2 | 2 | 1 | 3 | 6 | 6 | 7 | 12 | 6 | 10 | 10 |
|  | REPS | 2 | 2 | 2 | 4 | 1 | 3 | 6 | 6 | 7 | 14 | 6 | 10 | 10 |
|  | DIFF | 20.7 | 27 | 0.0 | 5.2 | 0.0 | 1.3 | 2.0 | 4.8 | 1.1 | 1.9 | 3.0 | 21 | 41 |
|  | PROB |  |  | 1.00 | .169 |  | .855 | .710 | .048+ | .084* | .258 | .566 | .035+ | .005# |

| DEPT | VAR # | POL SC ABS | TAS BLS ABS | TAS SZ ABS | TEX EAR ABS | TST WT ABS | GRN APP ABS | SCT GRN ABS | STA GRN ABS | EAR MLD ABS | NLF BLT ABS | ECB 1LF ABS | ECB 2SC ABS |
|---|---|---|---|---|---|---|---|---|---|---|---|---|---|
| TOTAL SUM | 1 | 4.5 | 9.0 | 4.5 | 7.0 | 52.7 | 7.0 | 9.0 | 6.0 | 9.0 | 8.0 | 7.0 | 3.0 |
|  | 2 | 5.5 | 9.0 | 4.8 | 7.0 | 52.8 | 6.0 | 7.5 | 5.0 | 9.0 | 7.0 | 7.0 | 6.0 |
|  | LOCS | 2 | 1 | 4 | 1 | 1 | 1 | 2 | 3 | 1 | 1 | 3 | 1 |
|  | REPS | 2 | 1 | 4 | 1 | 2 | 1 | 2 | 3 | 1 | 1 | 3 | 1 |
|  | DIFF | 1.0 | 0.0 | 0.3 | 0.0 | 0.2 | 1.0 | 1.5 | 1.0 | 0.0 | 1.0 | 0.0 | 3.0 |
|  | PROB | .500 |  | .718 |  |  |  | .205 | .580 |  |  | .000# |  |

TABLE 3C

PAIRED INBRED COMPARISON DATA
VARIETY #1-PHTE4
VARIETY #2-PHJ40

* = 10% SIG   + = 5% SIG   # = 1% SIG

| DEPT | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS | GDU SLK ABS | POL WT ABS |
|---|---|---|---|---|---|---|---|---|---|---|---|---|---|---|---|---|
| TO- | 1 | 77.2 | 99 | 6.1 | 23.2 | 6.2 | 96.8 | 77.9 | 29.2 | 5.9 | 42.3 | 99.6 | 2.7 | 1277 | 1275 | 131.0 |
| TAL | 2 | 64.2 | 83 | 5.3 | 17.4 | 4.8 | 94.5 | 63.4 | 27.2 | 5.8 | 41.4 | 99.7 | 1.1 | 1175 | 1185 | 111.3 |
| SUM | LOCS | 17 | 17 | 7 | 21 | 5 | 28 | 24 | 24 | 25 | 57 | 6 | 37 | 41 | 37 | 9 |
|  | REPS | 48 | 48 | 7 | 53 | 5 | 41 | 42 | 42 | 41 | 115 | 14 | 67 | 59 | 49 | 18 |

TABLE 3C-continued

PAIRED INBRED COMPARISON DATA
VARIETY #1-PHTE4
VARIETY #2-PHJ40

| | | | | | | | | | | | | | | | |
|---|---|---|---|---|---|---|---|---|---|---|---|---|---|---|---|
| | DIFF | 13.1 | 16 | 0.9 | 5.8 | 1.4 | 2.3 | 14.6 | 2.0 | 0.1 | 0.9 | 0.1 | 1.6 | 102 | 90 | 19.7 |
| | PROB | .001# | .002# | .172 | .000# | .005# | .131 | .000# | .030+ | .719 | .150 | .760 | .249 | .000# | .000# | .041+ |

| DEPT | VAR # | POL WT % MN | POL SC ABS | TAS BLS ABS | TAS SZ ABS | TEX EAR ABS | TST WT ABS | GRN APP ABS | SCT GRN ABS | STA GRN ABS | STK LDG ABS | RT LDG ABS | EAR MLD ABS | NLF BLT ABS | ECB 1LF ABS | ECB 2SC ABS |
|---|---|---|---|---|---|---|---|---|---|---|---|---|---|---|---|---|
| TO- | 1 | 104 | 5.3 | 9.0 | 4.7 | 7.0 | 57.9 | 6.3 | 8.2 | 5.7 | 97.3 | 98.9 | 7.4 | 5.4 | 6.2 | 4.2 |
| TAL | 2 | 86 | 4.9 | 9.0 | 4.5 | 7.5 | 59.4 | 6.1 | 6.8 | 2.2 | 97.3 | 98.2 | 6.0 | 4.5 | 3.4 | 3.8 |
| SUM | LOCS | 9 | 20 | 5 | 10 | 2 | 17 | 9 | 6 | 12 | 11 | 5 | 5 | 6 | 9 | 5 |
| | REPS | 18 | 32 | 9 | 10 | 2 | 47 | 19 | 6 | 21 | 27 | 12 | 5 | 7 | 9 | 6 |
| | DIFF | 18 | 0.3 | 0.0 | 0.2 | 0.5 | 1.4 | 0.1 | 1.3 | 3.4 | 0.0 | 0.7 | 1.4 | 0.9 | 2.8 | 0.4 |
| | PROB | .052* | .235 | 1.00 | .662 | .500 | .002# | .844 | .001# | .000# | .992 | .516 | .005φ | .403 | .001# | .688 |

TABLE 3D

PAIRED INBRED COMPARISON DATA
VARIETY #1-PHTE4
VARIETY #2-PHT46

* = 10% SIG   + = 5% SIG   # = 1% SIG

| DEPT | VAR # | YLD SC ABS | MST ABS | EAR SZ ABS | BAR PLT ABS | PLT HT ABS | EAR HT ABS | SDG VGR ABS | EST CNT ABS | TIL LER ABS | GDU SHD ABS | GDU SLK ABS | POL WT ABS |
|---|---|---|---|---|---|---|---|---|---|---|---|---|---|
| TOTAL SUM | 1 | 6.3 | 12.8 | 6.2 | 95.6 | 78.8 | 31.4 | 5.6 | 29.9 | 2.2 | 1268 | 1268 | 131.7 |
| | 2 | 5.0 | 12.0 | 5.2 | 90.6 | 62.3 | 25.5 | 5.6 | 28.7 | 2.3 | 1168 | 1167 | 83.1 |
| | LOCS | 8 | 2 | 5 | 16 | 11 | 11 | 17 | 35 | 20 | 29 | 29 | 4 |
| | REPS | 8 | 2 | 5 | 16 | 11 | 11 | 17 | 60 | 24 | 33 | 33 | 8 |
| | DIFF | 1.3 | 0.8 | 1.0 | 5.0 | 16.5 | 5.8 | 0.1 | 1.1 | 0.1 | 100 | 101 | 48.7 |
| | PROB | .011+ | .500 | .034+ | .228 | .000# | .049+ | .884 | .114 | .949 | .000# | .000# | .055* |

| DEPT | VAR # | POL WT % MN | POL SC ABS | TAS BLS ABS | TAS SZ ABS | TEX EAR ABS | GRN APP ABS | SCT GRN ABS | STA GRN ABS | EAR MLD ABS | NLF BLT ABS | ECB 1LF ABS | ECB 2SC ABS |
|---|---|---|---|---|---|---|---|---|---|---|---|---|---|
| TOTAL SUM | 1 | 115 | 5.3 | 9.0 | 4.6 | 7.0 | 7.0 | 8.3 | 5.0 | 7.4 | 5.2 | 6.3 | 4.3 |
| | 2 | 71 | 4.8 | 9.0 | 4.4 | 6.0 | 5.0 | 7.6 | 2.5 | 6.6 | 5.6 | 4.1 | 3.0 |
| | LOCS | 4 | 12 | 3 | 11 | 2 | 1 | 7 | 4 | 5 | 5 | 9 | 3 |
| | REPS | 8 | 16 | 5 | 11 | 2 | 1 | 7 | 4 | 5 | 5 | 9 | 3 |
| | DIFF | 45 | 0.5 | 0.0 | 0.3 | 1.0 | 2.0 | 0.7 | 2.5 | 0.8 | 0.4 | 2.2 | 1.3 |
| | PROB | .052* | .237 | 1.00 | .625 | .000# | | .220 | .030+ | .242 | .688 | .013+ | .057* |

TABLE 3E

PAIRED INBRED COMPARISON DATA
VARIETY #1-PHTE4
VARIETY #2-PHBW8

* = 10% SIG   + = 5% SIG   # = 1% SIG

| DEPT | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS |
|---|---|---|---|---|---|---|---|---|---|---|---|
| TOTAL SUM | 1 | 80.4 | 97 | 6.1 | 20.9 | 5.2 | 97.0 | 76.3 | 29.5 | 5.9 | 39.0 |
| | 2 | 92.0 | 111 | 6.4 | 22.0 | 6.4 | 97.4 | 72.6 | 29.5 | 5.9 | 39.5 |
| | LOCS | 16 | 16 | 10 | 22 | 10 | 25 | 31 | 31 | 34 | 61 |
| | REPS | 34 | 34 | 10 | 41 | 10 | 31 | 46 | 46 | 40 | 106 |
| | DIFF | 11.6 | 14 | 0.3 | 1.1 | 1.2 | 0.4 | 3.7 | 0.0 | 0.0 | 0.6 |
| | PROB | .000# | .000# | .541 | .008# | .005# | .642 | .002# | .978 | .911 | .341 |

| DEPT | VAR # | DRP EAR ABS | TIL LER ABS | GDU SHD ABS | GDU SLK ABS | POL WT ABS | POL WT % MN | POL SC ABS | TAS BLS ABS | TAS SZ ABS | TEX EAR ABS |
|---|---|---|---|---|---|---|---|---|---|---|---|
| TOTAL SUM | 1 | 99.7 | 2.9 | 1276 | 1274 | 134.8 | 100 | 5.1 | 9.0 | 4.6 | 6.3 |
| | 2 | 100.0 | 1.9 | 1278 | 1292 | 108.4 | 78 | 4.2 | 9.0 | 4.1 | 6.5 |
| | LOCS | 7 | 39 | 44 | 42 | 6 | 6 | 18 | 3 | 14 | 6 |
| | REPS | 16 | 58 | 56 | 52 | 12 | 12 | 27 | 5 | 16 | 6 |
| | DIFF | 0.3 | 0.9 | 02 | 18 | 26.5 | 22 | 0.9 | 0.0 | 0.5 | 0.2 |
| | PROB | .172 | .479 | .604 | .003# | .180 | .145 | .005# | 1.00 | .197 | .771 |

TABLE 3E-continued

PAIRED INBRED COMPARISON DATA
VARIETY #1-PHTE4
VARIETY #2-PHBW8

| DEPT | VAR # | TST WT ABS | GRN APP ABS | SCT GRN ABS | STA GRN ABS | STK LDG ABS | RT LDG ABS | EAR MLD ABS | NLF BLT ABS | STW WLT ABS | ECB 1LF ABS | ECB 2SC ABS |
|---|---|---|---|---|---|---|---|---|---|---|---|---|
| TOTAL SUM | 1 | 58.3 | 6.8 | 7.5 | 5.2 | 92.1 | 99.2 | 7.9 | 5.2 | 7.0 | 6.4 | 4.2 |
| | 2 | 55.7 | 5.6 | 7.1 | 5.1 | 92.1 | 94.7 | 7.9 | 5.8 | 7.0 | 4.3 | 4.8 |
| | LOCS | 14 | 7 | 12 | 14 | 12 | 7 | 10 | 9 | 1 | 15 | 5 |
| | REPS | 30 | 15 | 12 | 20 | 25 | 15 | 10 | 12 | 1 | 18 | 6 |
| | DSIFF | 2.5 | 1.3 | 0.4 | 0.1 | 0.0 | 4.5 | 0.0 | 0.6 | 0.0 | 2.1 | 0.6 |
| | PROB | .000# | .139 | .499 | .720 | .999 | .244 | .000# | .155 | | .000# | .426 |

TABLE 4A

AVERAGE INBRED BY TESTER PERFORMANCE COMPARING PHNV4 TO PHTE4 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

| | KINBRED | PRM PRM | SEL IND | BU ACR | YLD | MST | GDU SHD | PRM SHD | STK LDG | RT LDG | STA GRN | TST WTA | GRN APP |
|---|---|---|---|---|---|---|---|---|---|---|---|---|---|
| TOTAL | REPLIC. | 20 | 20 | 20 | 20 | 20 | 6 | 2 | 14 | 7 | 4 | 20 | 8 |
| MEAN WTS | PHNVR | 101 | 106 | 154 | 104 | 105 | 99 | 98 | 101 | 99 | 98 | 99 | 99 |
| MEAN WTS | PHTE4 | 101 | 117 | 166 | 111 | 106 | 100 | 99 | 100 | 96 | 89 | 100 | 101 |
| | DIFF. | | 11 | 12 | 7 | 0 | 1 | 1 | 0 | 3 | 9 | 1 | 2 |

| | KINBRED | SDG VGR | EST CNT | STK CNT | PLT HT | EAR HT | DRP EAR | BRT STK |
|---|---|---|---|---|---|---|---|---|
| TOTAL | REPLIC. | 9 | 14 | 20 | 9 | 9 | 4 | 2 |
| MEAN WTS | PHNV4 | 108 | 95 | 97 | 104 | 108 | 100 | 100 |
| MEAN WTS | PHTE4 | 113 | 103 | 103 | 98 | 95 | 100 | 99 |
| | DIFF. | 4 | 8 | 6 | 5 | 13 | | 1 |

TABLE 4B

AVERAGE INBRED BY TESTER PERFORMANCE COMPARING PHRE1 TO PHTE4 CROSSED TO THE SAME KINBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

| | KINBRED | PRM | SEL IND | BU ACR | YLD | MST | GDU SHD | PRM SDH | STK LDG | TST WTA | SDG VGR |
|---|---|---|---|---|---|---|---|---|---|---|---|
| TOTAL | REPLIC. | 12 | 12 | 12 | 12 | 12 | 3 | 1 | 8 | 12 | 6 |
| MEAN WTS | PHRE1 | 99 | 123 | 170 | 115 | 99 | 99 | 98 | 101 | 98 | 95 |
| MEAN WTS | PHTE4 | 101 | 119 | 168 | 113 | 109 | 101 | 100 | 101 | 100 | 117 |
| | DIFF. | 2 | 4 | 2 | 2 | 10 | 1 | 1 | 0 | 2 | 22 |

| | KINBRED | EST CNT | STK CNT | PLT HT | EAR HT | DRP EAR | BRT STK |
|---|---|---|---|---|---|---|---|
| TOTAL | REPLIC. | 8 | 12 | 4 | 4 | 4 | 2 |
| MEAN WTS | PHRE1 | 106 | 106 | 100 | 111 | 100 | 100 |
| MEAN WTS | PHTE4 | 104 | 103 | 99 | 94 | 100 | 99 |
| | DIFF. | 3 | 3 | 1 | 17 | | 1 |

TABLE 4C

AVERAGE INBRED BY TESTER PERFORMANCE COMPARING PHTE4 TO PHBW8 CROSSED TO THE SAME KINBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

| | KINBRED | PRM | SEL IND | BU ACR | YLD | MST | GDU SHD | PRM SHD | STK LDG | RT LDG | STA GRN | TST WTA | GRN APP | SDG VGR |
|---|---|---|---|---|---|---|---|---|---|---|---|---|---|---|
| TOTAL | REPLIC. | 166 | 176 | 181 | 181 | 182 | 60 | 15 | 151 | 83 | 71 | 170 | 122 | 72 |
| MEAN WTS | PHTE4 | 104 | 101 | 161 | 100 | 99 | 98 | 102 | 98 | 101 | 94 | 102 | 108 | 108 |

TABLE 4C-continued

AVERAGE INBRED BY TESTER PERFORMANCE COMPARING PHTE4 TO PHBW8 CROSSED TO THE SAME KINBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

| MEAN WTS | PHBW8 | 106 | 102 | 165 | 102 | 104 | 100 | 102 | 103 | 101 | 115 | 101 | 97 | 106 |
|---|---|---|---|---|---|---|---|---|---|---|---|---|---|---|
| | DIFF. | 2 | 1 | 4 | 2 | 5 | 1 | 0 | 4 | 0 | 21 | 1 | 12 | 3 |

| | | KINBRED | EST CNT | STK CNT | PLT HT | EAR HT | DRP EAR | BRT STK |
|---|---|---|---|---|---|---|---|---|
| | TOTAL | REPLIC. | 149 | 217 | 99 | 99 | 76 | 4 |
| | MEAN WTS | PHTE4 | 102 | 101 | 99 | 96 | 100 | 101 |
| | MEAN WTS | PHBW8 | 102 | 100 | 95 | 95 | 100 | 101 |
| | | DIFF. | 0 | 1 | 4 | 1 | 0 | 1 |

TABLE 5A

VARIETY #1-PHTE4 HYBRID
VARIETY #2-PHBW8 PYBRID

| | | | | | | * = 10% SIG | + = 5% SIG | # = 1% SIG | |
|---|---|---|---|---|---|---|---|---|---|
| DEPT | VAR # | PRM | PRM SHD | BU ACR ABS | BU ACR % MN | MST MST % MN | STK LDG % MN | RT LDG % MN | STA GRN % MN | TST WTA % MN |
| TOTAL SUM | 1 | 105 | 102 | 162.9 | 105 | 102 | 103 | 101 | 97 | 101 |
| | 2 | 106 | 101 | 163.4 | 104 | 105 | 104 | 102 | 105 | 101 |
| | LOCS | 13 | 7 | 47 | 47 | 47 | 39 | 22 | 16 | 45 |
| | REPS | 13 | 7 | 63 | 63 | 63 | 52 | 30 | 19 | 61 |
| | DIFF | 1 | 1 | 0.5 | 0 | 3 | 1 | 1 | 8 | 0 |
| | PROB | .005# | .375 | .868 | .830 | .003# | .192 | .670 | .216 | .298 |

| DEPT | VAR # | GRN APP % MN | SDG VGR % MN | EST CNT % MN | STK CNT % MN | PLT HT % MN | EAR HT % MN | DRP EAR % MN | BRT STK % MN | GDU SHD % MN |
|---|---|---|---|---|---|---|---|---|---|---|
| TOTAL SUM | 1 | 104 | 110 | 103 | 100 | 99 | 101 | 100 | 101 | 99 |
| | 2 | 104 | 112 | 102 | 100 | 93 | 95 | 100 | 99 | 99 |
| | LOCS | 25 | 22 | 27 | 53 | 18 | 18 | 23 | 1 | 15 |
| | REPS | 36 | 31 | 32 | 71 | 21 | 21 | 31 | 1 | 19 |
| | DIFF | 0 | 2 | 1 | 0 | 6 | 6 | 0 | 2 | 1 |
| | PROB | .964 | .578 | .506 | .643 | .000# | .011+ | .328 | | .278 |

TABLE 5B

VARIETY #1-PHTE4 HYBRID
VARIETY #2-PHRE1 HYBRID

| | | | | | | | | | * = 10% SIG | + = 5% SIG | # = 1% SIG | | |
|---|---|---|---|---|---|---|---|---|---|---|---|---|---|
| DEPT | VAR # | PRM | PRM SHD | BU ACR ABS | BU ACR % MN | MST % MN | STK LDG % MN | TST WTA % MN | SDG VGR % MN | EST CNT % MN | STK CNT % MN | PLT HT % MN | EAR HT % MN | GDU SHD % MN |
| TOTAL SUM | 1 | 101 | 99 | 167.7 | 113 | 108 | 101 | 100 | 116 | 104 | 103 | 99 | 94 | 101 |
| | 2 | 99 | 98 | 170.4 | 115 | 99 | 101 | 98 | 95 | 107 | 106 | 100 | 111 | 99 |
| | LOCS | 1 | 1 | 6 | 6 | 6 | 4 | 6 | 3 | 4 | 6 | 2 | 2 | 2 |
| | REPS | 1 | 1 | 12 | 12 | 12 | 8 | 12 | 6 | 8 | 12 | 4 | 4 | 3 |
| | DIFF | 2 | 1 | 2.7 | 2 | 10 | 0 | 2 | 21 | 3 | 3 | 1 | 17 | 2 |
| | PROB | | | .635 | .587 | .004# | .391 | .078* | .195 | .532 | .314 | .500 | .219 | .392 |

Industrial Applicability

The foregoing is set forth by way of example and is not intended to limit the scope of the invention.

This invention also is directed to methods for producing a corn plant by crossing a first parent corn plant with a second parent corn plant wherein the first or second parent corn plant is an inbred corn plant from the line PHTE4. Further, both first and second parent corn plants can come from the inbred corn line PHTE4. Thus, any such methods using the inbred corn line PHTE4 are part of this invention: selfing, backcrosses, hybrid production, crosses to populations, and the like. It also would include more unconventional methods of combining the inbred with another such as using various culturing techniques known to those skilled in the art. All plants produced using inbred corn line PHTE4 as a parent are within the scope of this invention. Advantageously, the inbred corn line is used in crosses with other, different, corn inbreds to produce first generation ($F_1$) corn hybrid seeds and plants with superior characteristics.

Corn plants (*Zea mays* L.) can be bred by both self-pollination and cross-pollination techniques. Corn has male flowers, located on the tassel, and female flowers, located on the ear, on the same plant. Natural pollination occurs in corn when wind blows pollen from the tassels to the silks that protrude from the tops of the incipient ears. Backcrossing can be used to transfer monogenic traits from on line to another. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

Hybrid corn seed is produced by planting male and female parental lines in sufficient proximity to permit pollination of the female line by the male line ("pollinating proximity"). To assure genetic uniformity and avoid self-pollination, steps are taken to prevent pollen formation by the plants of the parental line chosen to serve as the female. This is most commonly done by manual detasseling. Alternate strips of the parental lines of corn are planted in a field, and the pollen-bearing tassels are physically removed from the female plants, either by hand or by machine. Providing that there is sufficient isolation from other sources of corn pollen, the ears of the female plants will be fertilized only from pollen from the male plants, and the resulting seed is therefore hybrid and will form hybrid plants. In a single-cross hybrid, both parents are inbred lines. In a double-cross hybrid, both parents are the $F_1$ offspring of a cross of two inbred lines. In a three-way cross, one of the parents is an inbred line and the other parent is an $F_1$ hybrid. Each cross is made in the manner described herein.

Unfortunately, the manual detasseling process is not entirely reliable. Occasionally a female plant will be blown over by a storm and escape detasseling. Or, a detasseler will not completely remove the tassel of the plant. In either event, the female plant will successfully shed pollen and some female plants will be self-pollinated. This will result in seed of the female inbred being harvested along with the hybrid seed which is normally produced.

Alternatively, the female inbred can be mechanically detasseled. Mechanical detasseling is approximately as reliable as manual detasseling, but is faster and less costly. However, most detasseling machines produce more damage to the plants than manual detasseling.

The laborious detasseling process can be avoided by using cytoplasmic male-sterile (CMS) inbreds. Plants of a CMS inbred are male sterile (do not form pollen) as a result of cytoplasmic factors resulting from the cytoplasmic, as distinguished from the nuclear, genome. Thus, this characteristic is inherited exclusively through the female parent, since the female parent provides the cytoplasm of the fertilized seed. CMS plants are fertilized with pollen from another inbred that is not male-sterile. Pollen from the male parent may or may not contribute genes that make the hybrid plants male-fertile. Usually seed from detasseled normal maize and CMS-produced seed of the same hybrid must be blended to insure that adequate pollen loads are available for fertilization when the hybrid plants are grown.

There can be other drawbacks to CMS. One is an historically observed association of a specific variant of CMS with susceptibility to certain crop diseases. This problem has led to widespread abandonment of use of that CMS variant in producing hybrid maize. In addition, CMS sometimes has a negative association with agronomic performance, particularly in the areas of stalk quality, early seedling vigor, and yield. Finally, CMS exhibits on occasion the potential for breakdown of sterility in certain environments, rendering CMS lines unreliable for hybrid seed production.

Another form of sterility, genic male sterility, is disclosed in U.S. Pat. Nos. 4,654,465 and 4,727,219 to Brar et al. However, this form of genetic male sterility requires maintenance of multiple mutant genes at separate locations within the genome and requires a complex marker system to track the genes and make use of the system convenient.

Another form of male sterility is imparted in a manner by which expression of a transgene produces a "pollen-toxic" compound which blocks pollen formation in some manner.

Still another form of genetic male sterility uses an inducible promoter to regulate expression of a gene which is known to be critical in microsporogenesis, i.e., the production of pollen. The selected gene is cloned, its native promoter removed, and the modified gene is inserted into an expression sequence with an inducible promoter responsive to external control. Preferably, the promoter is one which responds to application of a specific non-phytotoxic chemical to the plant.

Using transformation and gene substitution, the "critical" gene is deleted from the genome of the plant and replaced by the genetically-engineered gene incorporated into the expression sequence with the inducible promoter. In this method, the inducible promoter is used to induce fertility, not sterility. The selected gene's promoter sequences are removed so that the gene is not transcribed and the plant is male sterile. When it is desired to increase the male-sterile plant, male fertility is restored by inducing expression of the critical gene with a specific non-phytotoxic chemical. Any of the foregoing methods and combinations thereof can be used to prevent pollen formation by the female parent of the hybrid.

As used herein, the term plant includes plant cells, plant protoplasts, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Duncan, Williams, Zehr, and Widholm, *Planta*, (1985) 165:322–332 reflects that 97% of the plants cultured which produced callus were capable of plant regeneration. Subsequent experiments with both inbreds and hybrids produced 91% regenerable callus which produced plants. In a further study in 1988, Songstad, Duncan & Widholm in *Plant Cell Reports* (1 988), 7:262–265 reports several media additions which enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter,* 60:64–65 (1986), refers to somatic embryogenesis from glume callus cultures and B. V. Conger, et al., *Plant Cell Reports,* 6:345–347 (1987) indicates somatic embryogenesis from the tissue cultures of maize leaf segments. Thus, it is clear from the literature that the state of the art is such that these methods of obtaining plants are "conventional" in the sense that they are routinely used and have a very high rate of success. It should also be clear that the term "regenerable cells" as used in the claims should be construed broadly to include any of the foregoing examples of regenerable cells, when they have the genotype of PHTE4.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottesville, Va. 1982, at 367–372) and in Duncan, et al., "The Production of Callus Capable of Plant Regeneration from Immature Embryos of Numerous Zea Mays Genotypes," 165 *Planta* 322–332 (1985). Thus, another aspect of this invention is to provide cells which upon growth and differentiation produce corn plants having the genotype of the inbred line PHTE4. Such plants, after self-pollination, will yield plants having the physiological and morphological characteristics of PHTE4.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch in the wet-milling industry and corn flour in the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHTE4, the plant produced from the inbred seed, the hybrid corn plant produced from the crossing of the inbred, hybrid seed, and various parts of the hybrid corn plant can be utilized for human food, livestock feed, and as a raw material in industry.

Although the foregoing invention has been described in some detail by way of illustration and example for the purposes of clarity and understanding, it will be obvious that certain changes and modifications may be practiced within the scope of the invention, as limited only by the scope of the appended claims.

Deposit Statement

Applicant has made a deposit of at least 2500 seeds of Inbred Corn Line PHTE4 with the American Type Culture Collection (ATCC), Rockville, Md. 20852 U.S.A., ATCC Deposit No. 97065. The seeds deposited with the ATCC on Feb. 22, 1995 were taken from the deposit maintained by Pioneer Hi-Bred International, Inc., 700 Capital Square, 400 Locust Street, Des Moines, Iowa 50309-2340 since prior to the filing date of this application. This deposit of the Inbred Corn Line PHTE4 will be maintained in the ATCC depository, which is a public depository, for a period of 30 years, or 5 years after the most recent request, or for the effective life of the patent, whichever is longer, and will be replaced if it becomes nonviable during that period. Additionally, Applicant has satisfied all the requirements of 37 C.F.R. §§1.801–1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of its rights granted under this patent or under the Plant Variety Protection Act (7 USC 2321 et seq.)

What is claimed is:

1. Inbred corn seed designated PHTE4 and having the genotype of ATCC Accession No. 97065.

2. A corn plant produced by the seed of claim 1.

3. A tissue culture of regenerable cells of a plant of the inbred corn line PHTE4 wherein the tissue regenerates plants having all of the physiological and morphological characteristics of PHTE4.

4. A tissue culture according to claim 3, the tissue culture selected from the group consisting of leaves, pollen, embryos, roots, root tips, anthers, silk, flowers, kernels, ears, cobs, husks and stalks, and cells and protoplasts thereof.

5. A corn plant regenerated from a tissue culture of a plant of inbred corn line PHTE4 and having all of the physiological and morphological of PHTE4.

6. Hybrid seed produced by:

(a) planting, in pollinating proximity, seeds of two parental lines, one of the parental lines being PHTE4, and the other parental line having a genotype different from PHTE4;

(b) cultivating corn plants resulting from said planting;

(c) preventing pollen formation by the plants of one of the parental lines;

(d) allowing natural cross pollinating to occur between said parental lines; and (e) harvesting seeds produced by the plants which do not form pollen.

7. Hybrid seed produced by hybrid combination of plants of inbred corn seed designated PHTE4 and having ATCC Accession No. 97065 and plants of a parental line having a genotype different from PHTE4.

8. Hybrid plants grown from seed of claim 7.

9. A tissue culture of the regenerable cells of the corn plant generated from seed produced by hybrid combination of plants of inbred corn seed designated PHTE4 and having ATCC Accession No.—and plants of a parental line having a genotype different from PHTE4.

* * * * *

UNITED STATES PATENT AND TRADEMARK OFFICE
CERTIFICATE OF CORRECTION

PATENT NO. : 5,453,564
DATED : September 26, 1995
INVENTOR(S) : Michael A. Chapman It is certified that error appears in the above-indentified patent and that said Letters Patent is hereby corrected as shown below:

In the claims, column 22:

Claim 9. A tissue culture of the regenerable cells of the corn plant generated from seed produced by hybrid combination of plants of inbred corn seed designated PHTE4 and having ATCC Accession No. 97065 and plants of a parental line having a genotype different from PHTE4.

Signed and Sealed this

Sixteenth Day of January, 1996

Attest:

BRUCE LEHMAN

*Attesting Officer*            *Commissioner of Patents and Trademarks*